United States Patent [19]

Bharucha et al.

[11] 4,248,780

[45] Feb. 3, 1981

[54] PROCESS FOR PREPARING AMPICILLIN

[75] Inventors: Kekhusroo R. Bharucha, Toronto; Heinrich M. Schrenk, Don Mills; Clarke E. Slemon, Toronto, all of Canada

[73] Assignee: Canada Packers Limited, Canada

[21] Appl. No.: 68,385

[22] Filed: Aug. 21, 1979

[51] Int. Cl.$^3$ .......................................... C07D 499/12
[52] U.S. Cl. .................................. 260/239.1; 544/16
[58] Field of Search ....................... 260/239.1; 544/16

[56] References Cited

U.S. PATENT DOCUMENTS

| | | | |
|---|---|---|---|
| 3,140,282 | 7/1964 | Johnson et al. | 260/239.1 |
| 3,351,597 | 11/1967 | Higgins | 260/239.1 |
| 3,478,018 | 11/1969 | Robinson et al. | 260/239.1 |
| 3,678,037 | 7/1972 | Robinson | 260/239.1 |
| 3,741,959 | 6/1973 | Looker et al. | 260/239.1 |
| 3,980,637 | 9/1976 | Grossman et al. | 260/239.1 |
| 4,053,360 | 11/1977 | Bouzard et al. | 260/239.1 |

FOREIGN PATENT DOCUMENTS 1459807  12/1976  United Kingdom ................ 260/239.1

OTHER PUBLICATIONS

Chemical Abstracts 61:663f, (1964).
Chemical Abstracts 61:1869b, (1964).
Chemical Abstracts 61:4361e, (1964).
Chemical Abstracts 61:4362a, (1964).
Chemical Abstracts 61:8315d, (1964).
Chemical Abstracts 61:13316a, (1964).
Chemical Abstracts 61:14680b, (1964).
Chemical Abstracts 62:1666e, (1965).
Chemical Abstracts 62:3890f, (1965).
Chemical Abstracts 62:15015b, (1965).
Chemical Abstracts 63:8386f-8369c, (1965).
Newman et al., Tethedron Letters, No. 34, pp. 3267-3269, (1967).
Merck Index, 8th Edition, Merck & Co., Rahway, N.J., p. 80, (1968).

*Primary Examiner*—Natalie Trousof
*Assistant Examiner*—Vera C. Clarke
*Attorney, Agent, or Firm*—Bacon & Thomas

[57] ABSTRACT

A process for preparing ampicillin trihydrate is disclosed which comprises acylating silylated 6-aminopenicillanic acid with D(−)-α-phenylglycylchloride hydrochloride directly in the silylation reaction mixture in the presence of urea as an acid acceptor, hydrolyzing the reaction product and precipitating ampicillin-trihydrate from the resulting aqueous solution. The amounts of reactants, in particular of solvents and water, are adjusted to provide good yields of a product of high purity.

19 Claims, No Drawings

PROCESS FOR PREPARING AMPICILLIN

BACKGROUND OF THE INVENTION

The general method for preparing ampicillin by acylating 6-aminopenicillanic acid (which in the following is abbreviated as 6-APA) with D(−)-α-phenylglycylchloride.HCl according to the overall equation

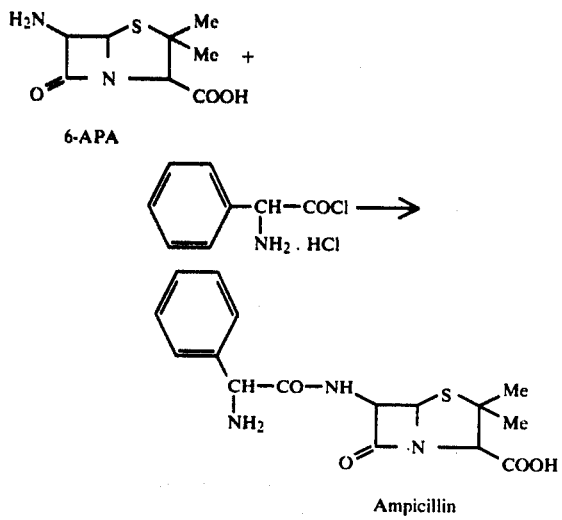

has long been known in the art.

A commonly used procedure for carrying out the above acylation of 6-APA, comprises silylating 6-APA with a silylating agent such as an organo-silyl chloride in the presence of an organic base such as triethylamine and a solvent, then coupling the silylated 6-APA with the phenylglycylchloride.HCl in the presence of a weak base and a solvent, hydrolyzing the resulting silylated ampicillin to remove the protective silyl group therefrom and isolating the formed ampicillin from the reaction mixture.

The key step in the conversion of 6-APA into ampicillin is the amide bond forming reaction in the presence of a weak base. The latter has to serve as an acid acceptor for the hydrochloric acid generated in this step, yet should not adversely affect the condensation reaction between the acyl chloride and the amino group of the silylated 6-APA. N,N-dimethylaniline has been found to be a suitable acid acceptor providing good yields of ampicillin on an industrial scale production. Unfortunately dimethylaniline is a cancer suspect agent and residual amounts of dimethylaniline or its hydrochloride in the final ampicillin product may provide a serious health hazard.

SUMMARY OF THE INVENTION

The present invention provides a process for preparing ampicillin from 6-APA using urea as a hydrogen halide acceptor rather than dimethylaniline, whereby health hazards due to impurities of a suspect nature are avoided. It has been proposed in U.S. Pat. No. 3,351,597 to use urea as a hydrogen halide acceptor in a process for acylating 7-aminocephalosporanic acid. However, when we attempted to use urea in the ampicillin reaction, we were unable to obtain satisfactory yields of high purity product. Many problems arose, including problems due to insolubility of the solid crystalline urea in polar solvents, the lumping of the reaction mass during the coupling of the α-phenylglycylchloride reagent with the silylated 6-APA, the decrease in yields when the amount of solvent was increased and the increase in impurities when the amount of solvent was decreased, difficulties in reaction control and in finding the proper solvents, solvent/dilutions and reaction conditions.

We have now discovered a process for preparing ampicillin from 6-APA, using urea as a hydrogen halide acceptor, which results in production of ampicillin trihydrate of acceptable purity in good yields. The process can be carried out in a simple one pot procedure wherein an ampicillin product of satisfactory purity is recovered without necessity of isolation of a crude substance which must then be subjected to further purification procedures in extraneous equipment.

Briefly, the process of the invention comprises acylation of a silylated 6-APA with a D(−)-α-phenylglycyl halide hydrogen halide in the presence of at least about 1.5 moles of urea per mole of 6-APA in an aprotic halogenated hydrocarbon solvent present in an amount of from about 1.5 to about 6 ml per 1 g of 6-APA while maintaining the temperature of the reaction mass below approximately 20° C., cooling the reaction mixture to a temperature of between about −5° to 5° C., mixing the cooled reaction mixture with at least about five times the theoretical amount of water to cleave the silyl groups and adjusting the pH to approximately 1.5 to 2.0 during this stage, raising the pH after cleavage of the silyl groups and precipitating ampicillin trihydrate.

The phenylglycyl halide may be the chloride or bromide and is preferably used in the form of an acid addition salt such as the hydrochloride or hydrobromide. Preferably, the phenylglycyl halide is D(−)-α-phenylglycylchloride.HCl. The reaction medium suitably is an aprotic halogenated hydrocarbon solvent, e.g. methylene chloride, chloroform or dichloroethane in which the silylated 6-APA is suspended or dissolved.

A more preferred process of the invention comprises the steps of:

(a) silylating 6-APA with an amount of between 0 and about 15% in excess of the stoichiometrically required amount of a silylating agent selected from the group consisting of trimethylmonochlorosilane, dimethyldichlorosilane and mixtures thereof in the presence of an amount of triethylamine which is sufficient to bind the hydrochloric acid generated during the silylating reaction and in the presence of an amount of from about 1.5 to about 6 ml per 1 g of 6-APA of a solvent selected from the group consisting of methylene chloride, chloroform and mixtures thereof, with the proviso that if the solvent is substantially comprised of methylene chloride the silylating agent is substantially comprised of trimethylmonochlorosilane, to form a silylated reaction mixture comprising a silylated 6-APA;

(b) cooling the silylated reaction mixture to a temperature of from about −30° to about 0° C.;

(c) mixing into the cooled reaction mixture at a temperature of between about −30° and about 0° C. an amount of about 1.5 to about 3 parts by mole of urea per 1 part by mole of 6-APA and an amount of between about 1 and 1.1 parts by mole of D(−)-α-phenylglycylchloride.HCl for a sufficient period of time to obtain a cooled condensation reaction mixture wherein the reactants are substantially uniformly distributed;

(d) gradually increasing the temperature of the cooled condensation reaction mixture to between about 10° and about 20° C. for a sufficient period of time to promote conversion of the silylated 6-APA into silylated ampicillin;

(e) maintaining the temperature of the condensation reaction mixture at a temperature of between about 10° and 20° C. for a sufficient period of time to complete transformation of the silylated 6-APA into silylated ampicillin;

(f) cooling the silylated ampicillin containing reaction mixture to a temperature of between about −5° and about 5° C.;

(g) mixing the cooled reaction mixture with water at a temperature of between about −5° and about 10° C. and adjusting the pH to approximately 1.5–2.0 in order to hydrolytically cleave the silyl groups without deterioration of the product and to obtain a reaction mixture comprising an organic phase and an aqueous phase containing the ampicillin dissolved therein, the amount of water being at least seven times the theoretical amount required to cleave the silyl groups;

(h) precipitating ampicillin trihydrate from the aqueous phase.

Further objects, features and advantages of the present invention will become apparent from the detailed description of the invention and its preferred embodiments which follow.

DETAILED DESCRIPTION OF THE INVENTION AND ITS PREFERRED EMBODIMENTS

The process according to the present invention comprises 4 reaction phases: silylation, amide-formation, hydrolytic desilylation, and neutralization which can, for example, be represented by the following reaction scheme which shows the reactants and main reaction products:

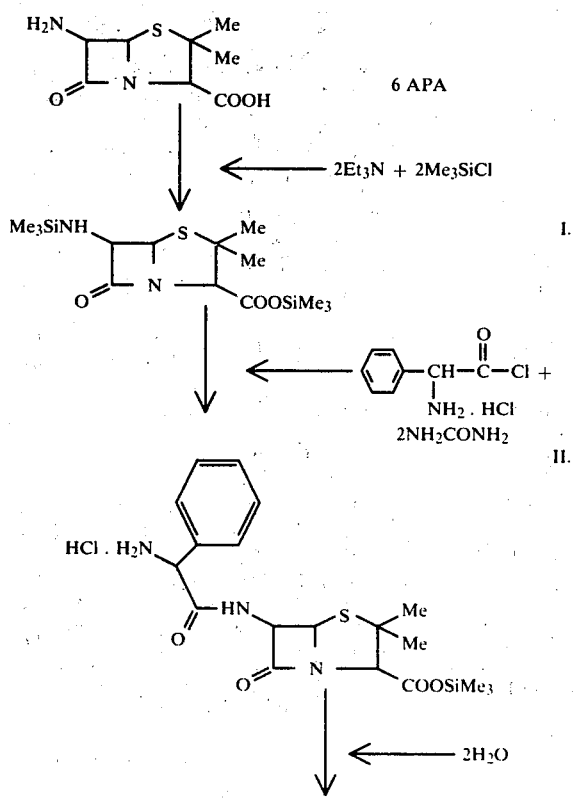

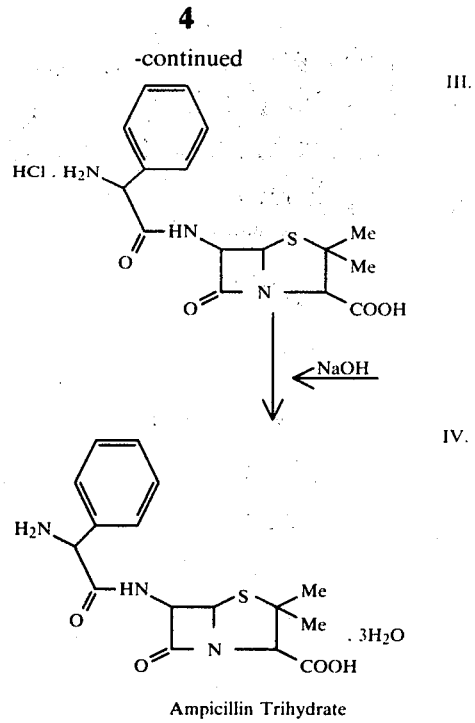

Ampicillin Trihydrate

According to the present invention all of these reactions are carried out without any intermediate separation of reaction products, preferably in a one-pot-procedure.

For the silylation of 6-APA two silanes, trimethylmonochlorosilane and dimethyldichlorosilane are used alone or in combination. The silylated 6-APA product is substantially comprised of disilylated 6-APA. If the silylating agent comprises dimethyldichlorosilane part of the silylated product may be in the form of dimers or polymers.

The silylating agent is suitably used in the stoichiometrically required amount or an excess thereof not exceeding 15%. The presence of higher excess amounts of silylating agent adversely affect the overall yield in ampicillin. Trimethylmonochlorosilane preferably is used in excess in an amount of between 2 and about 8%, most preferably in an excess amount of between about 3 and about 5% of the amount which is stoichiometrically required to obtain a disilylated 6-APA.

Unlike other acid acceptors, urea presents manipulative difficulties since in nonpolar organic solvents it remains an insoluble crystalline solid. During condensation of the silylated 6-APA with the phenylglycylchloride.HCl, there is a marked tendency for lump formation which is even more pronounced during the later addition of water.

In order to overcome these difficulties, according to the present invention methylene chloride, chloroform or mixtures thereof are used as a solvent for the silylating and the amide forming stages. Whereas all silylated 6-APA products, independently of which of the above silylating agents are used, are readily soluble in chloroform, silylated 6-APA products obtained with dimethyldichlorosilane appear to be only poorly soluble in methylenechloride. Therefore it is recommended in order to provide a sufficiently fluid reaction mixture, than when the solvent is substantially comprised of methylene chloride, the silylating agent be substantially comprised of trimethylmonochlorosilane.

The amount of solvent is not critical during the silylation stage but is critical during amide formation. It has been found that the overall yield of ampicillin is adversely affected if the subsequent amide formation is carried out in a too dilute reaction mixture and that lumping problems may occur if too little solvent is present. It is desirable that the amount of solvent present during the amide formation reaction be kept as low as possible consistent with physical manageability of the mixture.

In order to comply with the foregoing, it is advisable that the amount of solvent be within the range of between about 1.5 and about 6 ml of solvent per 1 g of 6-APA. At higher concentrations the reaction mass becomes increasingly pasty and difficult to handle whereas at lower concentrations the rate of amide formation and the overall yield in ampicillin decreases.

According to a preferred embodiment of the process trimethylmonochlorosilane is used as silylating agent and methylene chloride is used as a solvent. The amount of solvent used is below about 6 ml per 1 g of 6-APA but can be optimized to suit particular process conditions. For example, in laboratory runs the optimum amount may be less than in larger scale operations.

Triethylamine is used in the amount required to neutralize the hydrochloric acid generated during the silylation reaction. It is important that the triethylamine be substantially dry. Preferably about 2 moles of triethylamine are used per 1 mole of 6-APA.

The reaction temperature during the silylation suitably is between about 30° C. and reflux temperature of the reaction mixture. The silylation reaction mixture should reach this reaction temperature only after all reactants have been added thereto. Preferably the reaction mixture is then maintained at this reaction temperature for a silylation period of between about 1 and about 2 hours.

In a typical silylation procedure, triethylamine is added to a cooled suspension of 6-APA in the solvent, e.g., methylene chloride, and subsequently the silylating agent, e.g., trimethylmonochlorosilane, is added slowly, e.g., over a period of between about 25 and about 45 minutes, under sufficient cooling to allow only a gradual temperature rise and to prevent the temperature from reaching 35° C. prior to completion of the addition of the silylating agent. Subsequently the temperature is brought up to the final silylation temperature by the exothermicity of the reaction and/or additional heating. Depending on the size of the charge, it is advisable to cool the reactants prior to mixing same to a temperature of between −30° and 10° C., preferably −20° and −10° C.

In the following amide-formation, the silylated 6-APA product in the silylated reaction mixture is condensed with D(−)-α-phenylglycylchloride in the presence of urea to form a silylated ampicillin. Preferably 1 part by mole of the phenylglycylchloride or a slight excess of between about 3 and about 8% is used per 1 part by mole of 6-APA. The phenylglycylchloride is used in the form of an acid addition salt, preferably the hydrochloride.

Suitably about 1.5 to about 3, preferably about 2 parts by mole of urea are used per 1 part by mole of 6-APA. It is recommended that crystalline urea having a large surface and not prilled urea be used.

The total period during which the condensation is carried out is comprised of three segments: a low temperature period during which the reactants are mixed, a period of slow temperature increase and a period of a substantially constant temperature for completion of the reaction.

Firstly, the silylated reaction is cooled to a temperature of between about −30° and about 0° C. preferably between about −15° and about 0° C. and the urea and then the phenylglycylchloride.HCl are added and thoroughly mixed at a temperature of between about −30° and about 0° C. preferably between about −15° and about 0° C., most preferably between about −10° and about 0° C. In order to obtain a reaction mixture wherein all reactants are thoroughly intimately contacted and homogenized, mixing at this low temperature is carried out for a period of suitably between about 20 and about 70 minutes preferably between about 25 and 35 minutes. During this low temperature period the temperature is preferably maintained at a substantially constant value within the above mentioned range.

For small volumes of reaction mixture, cooling to a low temperature value of about 0° C. or slightly below, usually is satisfactory, whereas for larger industrial scale volumes, a lower temperature, e.g., a temperature of about −10° C. or below is preferred in order to avoid any premature heating up of the reaction mixture.

Subsequently, the temperature of the reaction mixture is allowed to slowly and gradually increase to a maximum temperature of between about 10° and about 20° C. over a period of suitably between about 30 and about 60 minutes, preferably between about 40 and about 50 minutes. As a temperature rise to about 0° C. initiates a strong exothermic reaction, vigorous cooling is needed to provide for an only gradual increase.

A substantially linear increase of temperature over the above period of time, e.g., over about 45 minutes is preferred but not essential.

Subsequently the temperature of the reaction mixture is maintained substantially constant at between about 10° and about 20° C., preferably between about 12° and about 18° C. over a period of preferably between about 20 and about 50 minutes, most preferably between about 25 and 45 minutes.

As mentioned before it is advisable that the amount of solvent be as small as is workable within the range of between about 1.5 and about 6 ml of solvent per 1 g of 6-APA starting material.

If desired, silylation can be carried out in a more highly concentrated reaction medium than the condensation and an additional amount of the solvent can be added after addition of the urea and the phenylglycylchloride salt. This procedure can advantageously be used when dealing with larger amounts of material, where addition of cooled solvent can contribute to cooling down the reaction mixture after the initial exothermic burst.

After completion of the condensation, the reaction mixture is cooled to a temperature of between about −5° about 5° C. for subsequent hydrolysis. The reaction mixture is hydrolyzed with water, preferably deionized water, at a temperature of between about −5° and about 10° C., preferably between about −2° and about 5° C. by mixing the organic reaction mixture with the water under stirring and cooling. Preferably the mixing takes place for a period of between about 15 minutes and about 60 minutes, most preferably between about 30 and 45 minutes.

In order to provide for sufficient fluidity of the reaction mixture, it is preferable to dilute the organic reaction mixture with additional solvent prior to mixing it with water. For example, an additional amount of organic solvent between about 1.5 and about 6 ml per 1 g of 6-APA starting material may be added.

If the reaction mixture is hydrolyzed with water alone, the resulting acidic aqueous phase, wherein the ampicillin is dissolved substantially in form of an acid addition salt, has a pH value of between 0.5 and about 0.8. In order to reduce the risk of decomposition during longer processing times which may be encountered in industrial scale production, it is advisable to adjust the pH value of the aqueous phase after hydrolysis has been initiated to between about 1.5 and about 2.5, preferably around 2.

To achieve product purity at least five and preferably seven times the theoretical amount of water needed to cleave the silyl groups (that is about 1.5 ml of water per 1 g of 6-APA starting material) is added. Then the pH value is adjusted to the desired value by addition of an alkaline aqueous solution preferably a 10% NaOH solution. It is preferable that the total amount of water added during the hydrolysis and the subsequent precipitation of ampicillin trihydrate be within the range of between about 7 and about 12 ml of water per 1 g of 6-APA starting material. Suitably the total amount of water added during the hydrolysis step in form of water as such and in form of an alkaline aqueous solution is between about 7 and about 12 ml, preferably about 9.5 ml per 1 g of 6-APA starting material.

The reaction mixture resulting from the hydrolysis comprises an organic phase and an acidic aqueous phase containing the ampicillin substantially dissolved therein in form of an acid addition salt. The ampicillin then is precipitated from the aqueous solution in the form of ampicillin trihydrate at about its isoelectric pH.

Preferably the organic phase is separated from the aqueous phase prior to precipitation of the ampicillin trihydrate.

An organic solvent which is substantially immiscible with water and in which the ampicillin trihydrate is not readily soluble may be added to the aqueous acidic phase prior to precipitation in order to reduce the content of organic impurities in the precipitated ampicillin trihydrate. Suitably such organic solvents are water immiscible ketones, in particular methylisobutylketone. For example, a small amount of methylisobutylketone, i.e. between about 0.25 and about 0.5 parts by volume relative to the volume of the aqueous phase may be used. Other organic solvents and different amounts may be used as a matter of choice.

Precipitation of the ampicillin trihydrate is effected by neutralizing the acidic aqueous solution to a pH value of between about 4.5 and about 5.3, preferably between about 5.1 and 5.2 by means of an aqueous alkaline solution, preferably an alkal hydroxide solution, e.g., a 20% NaOH solution.

Purity and yield of the final product are influenced by the volume of the aqueous phase from which the ampicillin trihydrate is precipitated. Precipitation from highly concentrated aqueous solutions leads to higher yields in precipitated solid ampicillin trihydrate, however the contents of impurities in the solid product are also increased. Precipitation from more dilute solutions leads to a purer product but also a lower yield. In order to obtain a satisfactory pure compound not requiring additional purification steps in good yields it is advisable to add to the aqueous solution a sufficient amount of water in order to obtain a total final amount of water of from about 7 to about 12 ml of water per 1 g of 6-APA starting material. Preferably the final total amount of water is from about 8.5 to about 11, most preferably from about 9 to about 10 ml of water per 1 g of 6-APA starting material.

Suitably, precipitation of the ampicillin trihydrate is carried out by continuously adding the required amount of alkali solution under stirring and then allowing the resulting suspension to stand for several hours at a temperature of between about 0° to about 15° C., preferably between about 3° and about 10° C. Subsequently the crystalline solid precipitate can readily be recovered by filtration or centrifugation, washed and dried to yield ampicillin trihydrate of high purity. Simple washing of the precipitate, e.g., with water and with acetone, is satisfactory and no additional purification steps are needed to achieve the high degree of purity which is mandatory for substances for medicinal use.

In order to favor the crystallization of ampicillin.3-$H_2O$ and to avoid gel formation in the initial precipitation stage, it is advisable to add a crystalline ampicillin.$3H_2O$ seeding material prior to starting the precipitation or shortly after precipitation has been induced, e.g., a pH of between about 2 and about 3.2 has been reached. An amount of seeding material of between about 0.1 to about 0.3% by weight relative to the amount of starting 6-APA usually is satisfactory.

The following examples are given to further illustrate the invention without limiting it.

All temperatures given in the Examples are in degrees Centigrade.

EXAMPLE I

A suspension of 6-APA (107.15 g, 49.547 mmol) in methylene chloride (200 ml, 1.9 ml/g of 6-APA) was stirred at −10° C. in a reaction vessel. Triethylamine (138 ml) was added over 10 minutes and the mixture stirred for 5 minutes. Trimethylchlorosilane (132 ml 98% pure, 4% molar excess) was added over 45 minutes with cooling such that the heat of reaction gradually brought the reaction mixture to 35° C. at the end of the addition. The reaction product appeared as a white fluffy suspension. The mixture was stirred for two hours without temperature control and was then cooled to 0° C. or slightly below at which point urea (59.5 g, 2 molar ratio) was added followed by D-(−)-α-phenylglycylchloride hydrochloride (109.15 g, 7% excess). Stirring was continued while maintaining the temperature of the reaction mass at 0° C. for 30 minutes. The product at this point was of pasty consistency. The temperature was then raised to 15° C. (over 45 minutes) and held at this temperature for 25 minutes. Methylene chloride (200 ml, 5° C.) was added and the diluted reaction mixture cooled to −2° C., whereupon 290 ml of distilled deionized water was added quickly. This caused a momentary thickening then transition to a fluid coagulate which was stirred 5 minutes at 0° C. Then a solution of sodium hydroxide (23.5 g in distilled, deionized water 235 ml) at 5° C. was added over 5 minutes, causing the temperature to rise from −2° C. to +3° C. The mixture (one phase liquid) was stirred 5 minutes and then poured into a cooled separatory funnel and kept at 0° C. for 30 minutes. During this time the mixture separated into two phases. The organic layer (430 ml) and an interfacial layer (∼90 ml) were removed. The latter, on standing, freed more (30 ml) organic liquid. The residual emulsion was combined with the aqueous phase and filtered to give 850 ml of yellow solution, pH 2.0.

The aqueous layer was diluted with cold, distilled, deionized water (500 ml) and with cold methylisobutylketone (500 ml); stirred at 0°-3° C. and seeded with pure ampicillin trihydrate. The pH was adjusted with 20% NaOH to pH 5.1 (ca 100 ml). The precipitate was refrigerated (5° C.) overnight, filtered with suction, and washed first with cold distilled deionized water (2×125 ml) and then with cold acetone (2×175 ml). The product (ampicillin trihydrate) was dried in a forced-air dryer at 40° C. to constant weight 171.98 g, 86.0% yield, 1.605×wt. of 6-APA. Weight loss on drying 13.3, 13.5%. Acid-base concordance 3.0, 3.8.

EXAMPLE II

Into a 50 gallon stainless steel reactor, equipped with a jacket for coolant flow, was placed under nitrogen 19.07 lbs. of 6-APA and 20 l of cold methylene chloride. The charge was stirred slowly and cooled at −10° C. Over 13 minutes 11.18 l of triethylamine was added, followed after 5 minutes by 10.65 l of trimethylchlorosilane added over a period of 40 minutes during which the temperature of the reaction mass was permitted to rise to 29° C. The temperature was then raised to 35° C. The silylating mixture was continuously stirred. After 85 minutes the temperature was 32° C. The reaction mass was then cooled to −10° C. and 10.59 lb of cold urea and 19.46 lb of D(−)-α-phenylglycylchloride hydrochloride were added. The mixture was stirred intermittently at a temperature of about −15° C. to achieve homogenization and intimate contact. After 15 minutes, the temperature of the mixture was raised and after 25 minutes the temperature was about −5° C.

The exothermic reaction soon set in. Maximum cooling was provided during the first 20 minutes of the temperature rise. During this period the temperature rapidly rose up to 17° C. within about 4 minutes, and after 7 minutes started to decline again reaching about 7° C. after 20 minutes. The temperature was then slowly brought up to 15° C. over a period of 25 to 30 minutes.

The temperature was held at +15° C.±2° for 25 minutes, and then the full cooling was applied. The mixture was diluted with (−10° C.) methylene chloride (16 l), 25 minutes after the cooling was started. When the mixture reached +4° C. 23 l of ice-cold water was added to the mixture. The resultant temperature of the mixture was 2° C. The nitrogen flow was cut and stirring was continued for 15 minutes. A cold solution of sodium hydroxide (1.9 kg) in water (19 l) was added portion-wise over seven minutes. The temperature rose from −3° to +4° C. Stirring was continued.

The contents of the reaction vessel were transferred to a cooled 50 gallon open vessel and allowed to stand for an hour to let the phases separate. The lower organic layer (8 gallon) was removed. About 6 l of interface material was removed and allowed to stand in a separatory funnel. Meanwhile all the clear aqueous material was filtered. The aqueous interfacial material was separated from any methylene chloride and filtered last. The pH of the filtered liquid was 1.9-2.1. Forty liters of cold water was added (pH 1.8) and forty liters of methyl isobutylketone at −10° C. After seeding with 30 g of pure ampicillin, a 20% sodium hydroxide solution at −10° C. was slowly added. The pH went to 5.5 and was readjusted with 3:1 v/v concentrated HCl back to 5.1. The precipitate was let to stand overnight with cold water cooling. The next day the material was centrifuged, washed with cold water (20 l) and acetone (28 l) and dried at about 40° C. with an air flow. The yield was 30.24 lb (85.00%), 1.59×wt. of 6-APA.

What is claimed is:

1. A process for preparing ampicillin comprising, acylating silylated 6-aminopenicillanic acid with phenylglycyl halide in the presence of at least about 1.5 moles of urea per mole of 6-aminopenicillanic acid in an aprotic halogenated hydrocarbon solvent present in an amount of from about 1.5 to about 6 ml per 1 gram of 6-aminopenicillanic acid while maintaining the temperature of the reaction mass below about 20° C., cooling the reaction mixture to a teperature of between about −5° to 5° C., mixing the cooled reaction mixture with at least about five times the theoretical amount of water to cleave the silyl groups and adjusting the pH to approximately 1.5 to 2.0 during this stage, and after cleavage of the silyl groups raising the pH and precipitating ampicillin trihydrate.

2. The process of claim 1, wherein the phenylglycyl halide is D(−)-α-phenylglycylchloride.HCl and the aprotic halogenated hydrocarbon solvent is methylene chloride.

3. A process for preparing ampicillin which comprises the steps of
 (a) silylating 6-aminopenicillanic acid with an amount of between 0 and about 15% in excess of the stoichiometrically required amount of a silylating agent selected from the group consisting of trimethylmonochlorosilane, dimethyldichlorosilane and mixtures thereof in the presence of an amount of triethylamine which is sufficient to bind the hydrochloric acid generated during the silylating reaction and in the presence of an amount of from about 1.5 to about 6 ml per 1 g of 6-aminopenicillanic acid of a solvent selected from the group consisting of methylene chloride, chloroform and mixtures thereof with the proviso that if the solvent is substantially comprised of methylene dichloride the silylating agent is substantially comprised of trimethylmonochlorosilane to form a silylated reaction mixture comprising a silylated 6-aminopenicillanic acid;
 (b) cooling the silylated reaction mixture to a temperature of from about −30° to about 0° C.;
 (c) mixing into the cooled reaction mixture at a temperature of between about −30° and about 0° C. an amount of about 1.5 to about 3 parts by mole of urea per 1 part by mole of 6-aminopenicillanic acid and an amount of between about 1 and about 1.1 parts by mole of an acid addition salt of D(−)-α-phenylglycylchloride per 1 part by mole of 6-aminopenicillanic acid for a sufficient period of time to obtain a cooled condensation reaction mixture wherein the reactants are substantially uniformly distributed;
 (d) gradually increasing the temperature of the cooled condensation reaction mixture to between about 10° to about 20° C.;
 (e) maintaining the temperature of the condensation reaction mixture at a temperature of between about 10° and about 20° C. for a sufficient period of time to complete condensation of the silylated 6-aminopenicillanic acid into silylated ampicillin;
 (f) cooling the silylated ampicillin containing reaction mixture to a temperature of between about −5° and about 5° C.;
 (g) mixing the cooled reaction mixture with water at a temperature of between about −5° and about 10° C. in order to hydrolytically cleave the silyl groups and to obtain a reaction mixture comprising an organic phase and an acidic aqueous phase containing the ampicillin dissolved therein; and (h) precipitating ampicillin trihydrate from the aqueous phase.

4. The process as defined in claim 3, wherein the silylating agent is trimethylmonochlorosilane and the solvent is methylene chloride.

5. The process as defined in claim 3, wherein the mixing in step (c) takes place over a period of between about 20 and about 70 minutes, the increasing of the temperature in step (d) takes place over a period of between about 30 and about 60 minutes and in step (e) the temperature is maintained at between about 10° and about 20° C. for a period of between about 20 and about 50 minutes.

6. The process as defined in claim 5, wherein the mixing in step (c) takes place over a period of between about 25 minutes and about 35 minutes, the increasing of the temperature in step (d) takes place over a period of between about 40 and about 50 minutes and in step (e) the temperature is maintained at between about 10 and about 20° C. for a period of between about 25 and about 45 minutes.

7. The process as defined in claim 1, wherein the temperature of the acylation reaction mixture is initially between about −30° and 0° C.

8. The process as defined in claim 3, wherein in step (e) the temperature is between about 12° and about 18° C.

9. The process as defined in claim 1, wherein the amount of urea is about 2 parts by mole per 1 part by mole of 6-aminopenicillanic acid.

10. The process as defined in claim 3, wherein step (f) further comprises diluting the reaction mixture with additional solvent prior to mixing it with the water.

11. The process as defined in claim 3, wherein in step (g) after hydrolysis has been initiated, the pH-value of the acidic aqueous phase is adjusted to between about 1.5 and about 2.0.

12. The process as defined in claim 3, wherein step (g) comprises mixing into the reaction mixture an amount of water which is at least about 7 times the amount of stoichiometrically required for cleavage of the silyl groups and subsequently a sufficient amount of an alkaline aqueous solution to obtain an acidic aqueous phase having a pH-value of between about 1.5 and about 2.0.

13. The process as defined in claim 12, wherein the alkaline aqueous solution is a 10% NaOH solution.

14. The process as defined in claim 3, wherein step (g) comprises adding to the acidic aqueous phase a sufficient amount of water and a sufficient amount of an aqueous alkaline solution to obtain a final total amount of water of from about 7 to about 12 ml per 1 g of 6-aminopenicillanic acid and a final pH-value of between about 4.5 and about 5.3 in the aqueous phase.

15. The process as defined in claim 14, wherein the final total amount of water is from about 9 to about 10 ml per 1 g of 6-aminopenicillanic acid.

16. The process as defined in claim 3, wherein step (h) comprises separating the organic phase from the aqueous phase prior to the precipitating.

17. The process as defined in claim 16, which further comprises adding methyl isobutylketone to the aqueous phase prior to precipitating.

18. In a process for preparing ampicillin from 6-aminopenicillanic acid which comprises silylating 6-aminopenicillanic acid to obtain a silylated 6aminopenicillanic acid, acylating the silylated 6-aminopenicillanic acid with a D(−)-α-phenylglycyl halide to obtain a silylated ampicillin, and hydrolytically splitting of the silyl groups and recovering ampicillin trihydrate the improvement which comprises contacting the silylated 6-aminopenicillanic acid with an acid addition salt of the D(−)-α-phenylglycyl halide in a halogenated hydrocarbon solvent in the presence of urea.

19. The process as defined in claim 18, the improvement which comprises the steps of:

(a) mixing into a silylation reaction mixture comprising a silylated 6-aminopenicillanic acid and an amount of from about 1.5 to about 6 ml per 1 g of 6-aminopenicillanic acid of a solvent selected from the group consisting of methylene chloride, chloroform and mixtures thereof at a temperature of between about −30° and about 0° C. an amount of about 1.5 to about 3 parts by mole of urea per 1 part by mole of 6-aminopenicillanic acid and an amount of between about 1 and about 1.1 parts by mole of D(−)-α-phenylglycylchloride.HCl per 1 part by mole of 6-aminopenicillanic acid for a sufficient period of time to obtain a cooled condensation reaction mixture wherein the reactants are substantially uniformly distributed;

(b) gradually increasing the temperature of the cooled condensation reaction mixture to between about 10° and about 20° C.; and (c) maintaining the temperature of the condensation reaction mixture at a temperature of between about 10° and about 20° C. for a sufficient period of time to complete condensation of the silylated 6-aminopenicillanic acid into silylated ampicillin.

* * * * *

UNITED STATES PATENT AND TRADEMARK OFFICE
CERTIFICATE OF CORRECTION

PATENT NO. : 4,248,780
DATED : Feb. 3, 1981
INVENTOR(S) : Bharucha et al.

It is certified that error appears in the above—identified patent and that said Letters Patent is hereby corrected as shown below:

Column 1, line 68: "polar" should read -- non-polar --.

Column 4, line 64: "than" should read -- that --.

Column 6, line 56: "-5° about 5°C." should read -- -5° and about 5°C. --.

Signed and Sealed this

Sixth Day of October 1981

[SEAL]

Attest:

Attesting Officer

GERALD J. MOSSINGHOFF

Commissioner of Patents and Trademarks